US 6,413,394 B1

(12) United States Patent
Shen

(10) Patent No.: US 6,413,394 B1
(45) Date of Patent: Jul. 2, 2002

(54) DISPOSABLE PLATE ELECTRODE WITH BIOLOGICAL ACTIVE FILM

(76) Inventor: Thomas Y. Shen, 2F, No. 1, Alley 3, Lane 56, Sec. 4, Ming-Shen E Rd., Taipei (TW)

( * ) Notice: Subject to any disclaimer, the term of this patent is extended or adjusted under 35 U.S.C. 154(b) by 0 days.

(21) Appl. No.: 09/348,824

(22) Filed: Jul. 8, 1999

(51) Int. Cl.[7] ............................................. G01N 27/26
(52) U.S. Cl. ...................................... 204/403; 204/418
(58) Field of Search ................................ 204/403, 418, 204/415; 427/2.13

(56) References Cited

U.S. PATENT DOCUMENTS

| | | | | |
|---|---|---|---|---|
| 4,324,858 A | * | 4/1982 | Goodson et al. | 435/20 |
| 5,288,636 A | * | 2/1994 | Pollmann et al. | 435/287.9 |
| 5,773,270 A | * | 6/1998 | D'Orazio et al. | 435/17 |
| 5,958,201 A | * | 9/1999 | Craig et al. | 204/418 |
| 6,197,290 B1 | * | 3/2001 | Goto et al. | 424/78.1 |
| 6,258,230 B1 | * | 7/2001 | Shen et al. | 204/415 |

OTHER PUBLICATIONS

White et al. ("Development of a mass–producible glucose biosensor and flow–injeciton analysis system suitable for on–line monitoring during fermentation" Analytica Chimica Acta, 321 (1996 165–172) month unknown.*

Hart et al. ("Estimation of lactate in meat extracts by screen–printed sensors", Analytica Chimica Acta, 386 (Apr., 1999) 7–12.*

Collier et al. ("Estimaiton of soluble L–lactate in dairy products using screen–printed sensors in a flow injection analyser", Biosensors & Bioelectronics vol. 13, No. 2, pp. 219–225, 1998) month unknown.*

* cited by examiner

Primary Examiner—T. Tung
Assistant Examiner—Alex Noguerola
(74) Attorney, Agent, or Firm—Bacon & Thomas, PLLC

(57) ABSTRACT

A disposable plate electrode with biological active film is used to cooperate with a biological sensor for analyzing composition and measuring concentration of a test sample according to electric effect resulted from a biochemical reaction. The plate electrode comprises at least an electrode portion for transmission of the electric effect as well as a biological active film that reacts with the test sample chemically or biochemically. The biological active film contains a carrier layer (cellulose, for example) for adsorbing and keeping the biological active substance (enzyme, for example), which, the carrier layer, can change the electrode portion from hydrophobic into hydrophilic and protect the biological active substance against impairment during relatively higher temperature drying process. The method for forming a biological active film on the disposable electrode is mainly based on screen printing technique to form a conductive film, an electric insulating layer, a carrier layer, etc, for speedy production and low cost purpose.

13 Claims, 6 Drawing Sheets

DISPOSABLE PLATE ELECTRODE WITH BIOLOGICAL ACTIVE FILM

BACKGROUND OF THE INVENTION

This invention relates to a disposable plate electrode with biological active film and manufacture method thereof, particularly to a manufacture method that can produce plate electrode speedily and to a disposable plate electrode which is used to cooperate with a biosensor for composition analysis and concentration measurement of a test sample in accordance with the electrical output resulted from biochemical reaction.

The biochemistry analyzer is usually classified into three categories, namely, the wet type analyzer, the dry type analyzer, and the biosensor. Application of a conventional wet type biochemistry analyzer is to mix a test sample with reagent (a chromatic agent is commonly contained) for chemical reaction, then an optical reading device, such as a calorimeter or a spectrophotometer, is used to read color change before and after the reaction. This test way is weak at: a pre-treatment required for the test sample; difficulties in dosing and keeping a reagent valid for a long period; expensive instruments; and unfeasibility for non-professional operation, so that it fits a hospital or an examining center for mass sample analyses better than few quantity or emergency tests.

As to application of the dry type biochemistry analyzer, a test strip is coated on its surface with a chemical reagent, such as an enzyme, or antibody, etc to contact directly and react with the test sample for analysis. Though this test way can save dosing and adding process of the reagent, color of the test strip may be changed due to oxidation to affect color judgment before and after reaction.

The biosensor is composed of a biological element, a thin film element, and a sensor, wherein the biological element is made from biological material with cognizable specialties, such as microbe, cell, tissue, enzyme, antigen, and antibody, etc; the thin film element is usually made from polymeric material and used to fix the biological element and sieve out interference substance; and, the sensor may comprise electrodes, ion selective field effect transistors, thermistors, piezoelectric devices, optical fiber, photoelectric tubes, and sound wave counters, etc., and wherein the hydrogen peroxide electrode is the one most widely used.

Take the biosensor for analyzing blood glucose for instance, glucose is oxidized and fixed on a thin film, which is clad tightly on surface of a pillar hydrogen peroxide electrode, then a polarized potential is applied to the platinum anode and the silver/silver chloride cathode, the hydrogen peroxide produced by oxidation of the glucose will continue to be oxidized to water near surface of the anode, and meanwhile, release electrons. The glucose concentration of the test sample may be calculated according to the released amount of electrons.

The aforesaid pillar electrodes shall require constant refreshment including polishing, film clothing, cleaning, and recalibrating, etc, which may incur cross pollution owing to carelessness in addition to inconvenient implementation, not to mention the high production cost. For eliminating above defects, the U.S. Pat. No. 4,545,382 of Genetics International in UK has disclosed a blood glucose meter "Exactech" which is the first commercially realized example of a plate electrode in this field.

In U.S. Pat. No. 5,120,420—Biosensor and process for preparation thereof, another disclosed biological detecting plate electrode comprises an electrode portion, an insulation layer, a reaction layer, and a test sample bearing space on the reaction layer, wherein a sample inlet port and an gas exhaust port are provided to the bearing space. The reaction layer is formed by coating subsequently CMC (Carboxymethyl Cellulose) water solution on the electrode substrate to form a CMC layer, water solution of GOD (Glucose Oxidase), and then a suspending liquid containing conductive mediator to form a biochemistry reaction portion. Finally, a resin plate and a top plate are used to cover on the substrate to form the sample bearing space and complete thereby the biological detecting plate electrode.

The biochemistry reaction portion of the aforesaid U.S. Pat. No. 5,120,420 is formed in 3 steps, namely:

1. The CMC layer used to improve hydrophobicity of the carbon electrodes.
2. The GOD layer.
3. The conductive mediator layer.

Each step requires drying before completed.

SUMMARY OF THE INVENTION

This invention is proposed to provide a new fabrication process for plate electrode, which is provide at least with an electrode portion used to transmit electrical effect produced from biological reaction; and a biological active layer used to conduct a chemical or biochemical reaction with a test sample. The biological active layer comprises at least 3 portions: an absorptive carrier layer, an enzyme, and a conductive mediator. The carrier is printed on surface of the electrode portion with screen-printing technique and used to suck and sustain the biological active substance (such as enzyme) and the conductive mediator. Also, the carrier can turn the electrode portion from hydrophobic into hydrophilic, and moreover, protect the biological active substance against impairment in relatively high temperature drying process to make a speedy production of the plate electrode become possible.

Another object of this invention is to provide a simplified process for production of the plate electrode, wherein the carrier layer is printed on an insulating substrate of the plate electrode with screen-printing technique.

BRIEF DESCRIPTION OF THE DRAWINGS

For a better understanding to the present invention, together with further advantages or features thereof, at least one preferred embodiment will be elucidated below with reference to the annexed drawings in which.

DETAILED DESCRIPTION OF THE PREFERRED EMBODIMENT

Figure 1:
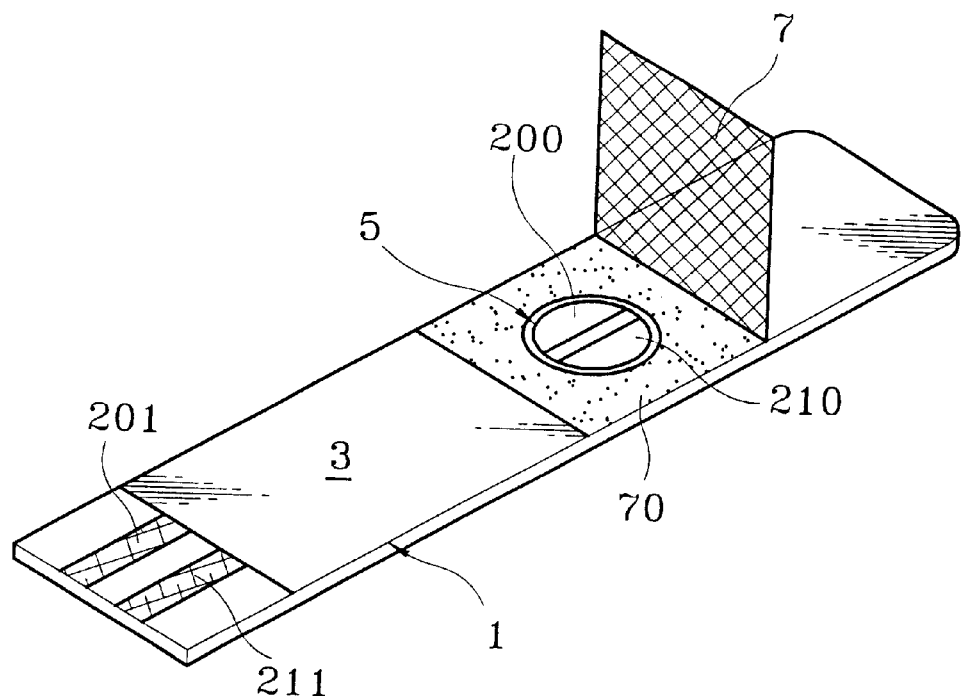
FIG. 1 is an elevational view showing structure of a plate electrode of this invention.
Figure 2:
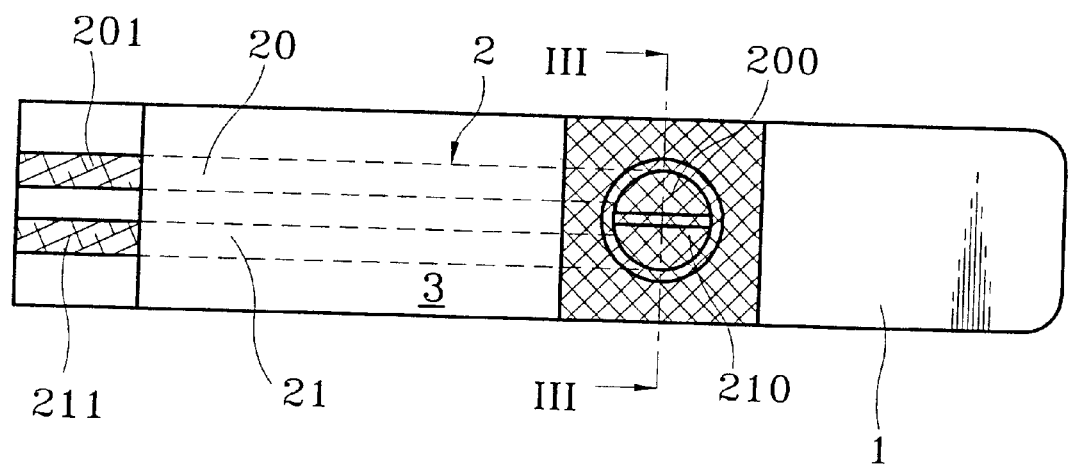
FIG. 2 is a front view showing structure of the plate electrode of this invention.
Figure 3:
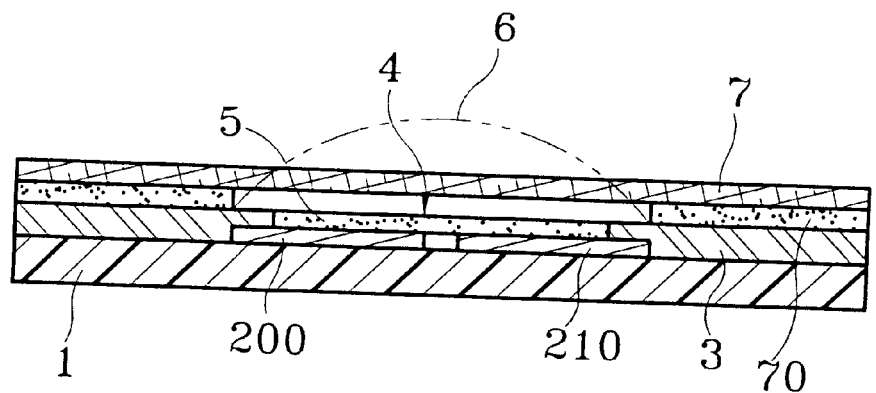
FIG. 3 is a cutaway sectional structure along line III—III in FIG. 2 of the plate electrode of this invention.
Figure 4A:
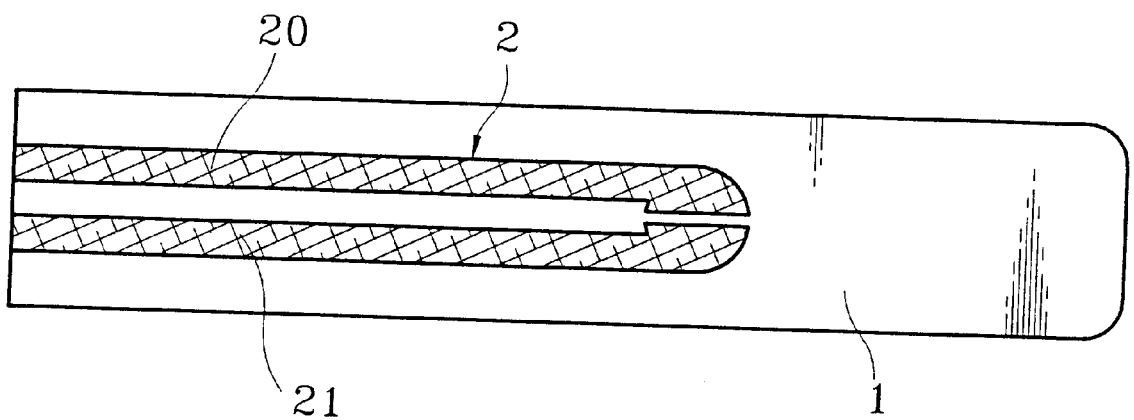
FIGS. 4A through 4H show production flow charts of this invention in preparation steps.
Figure 4B:
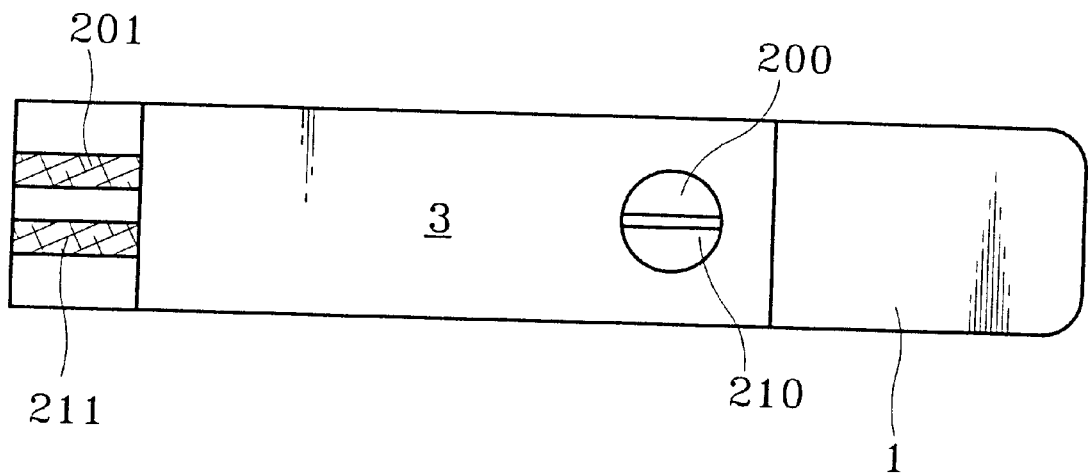
Figure 4C:
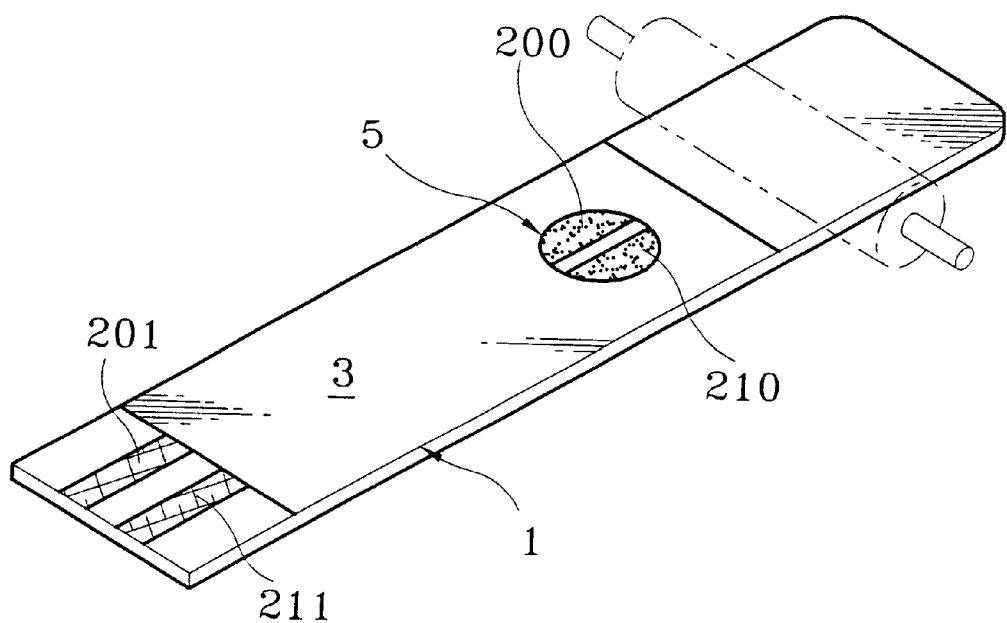
Figure 4D:
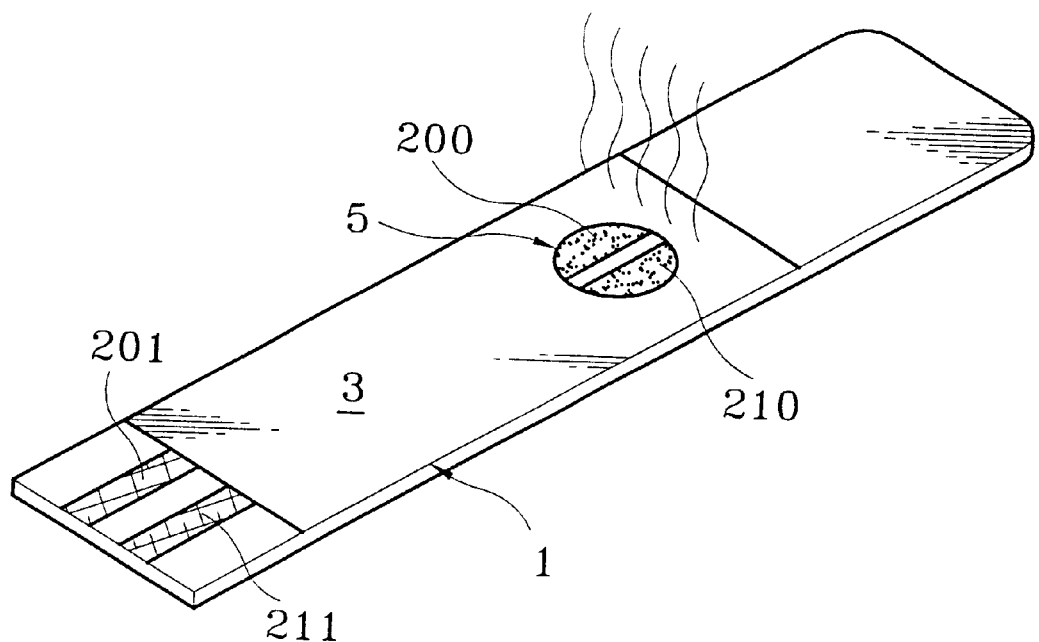
Figure 4E:
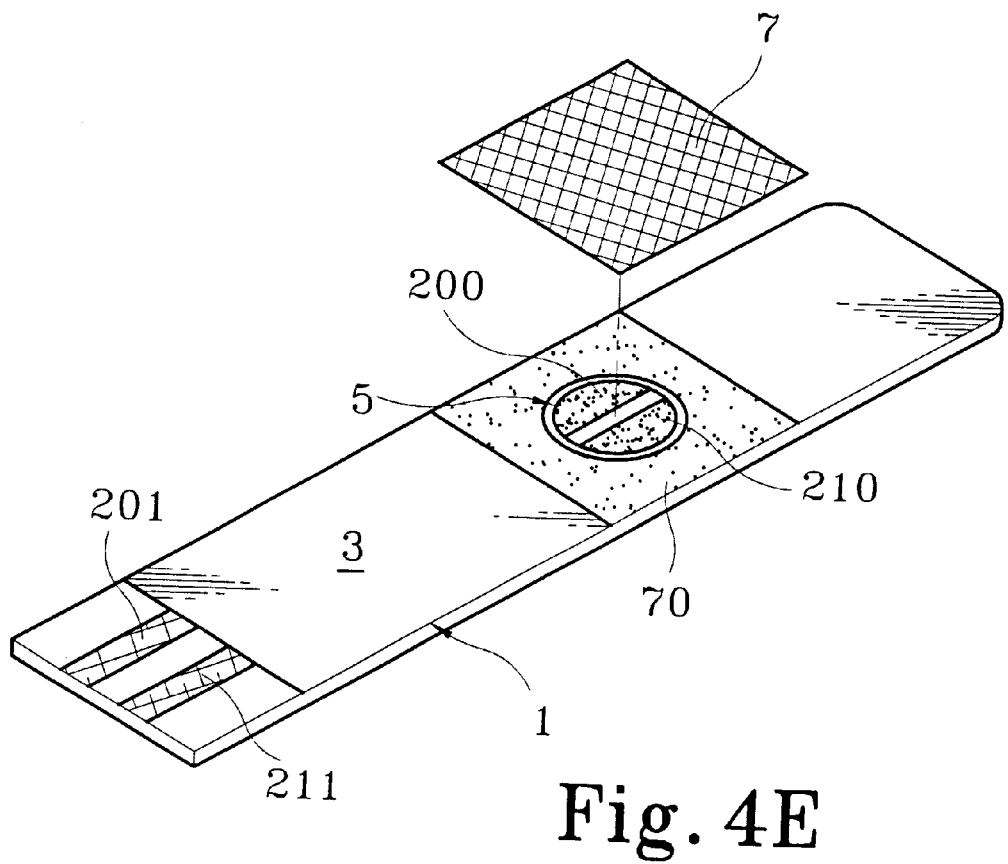
Figure 4F:
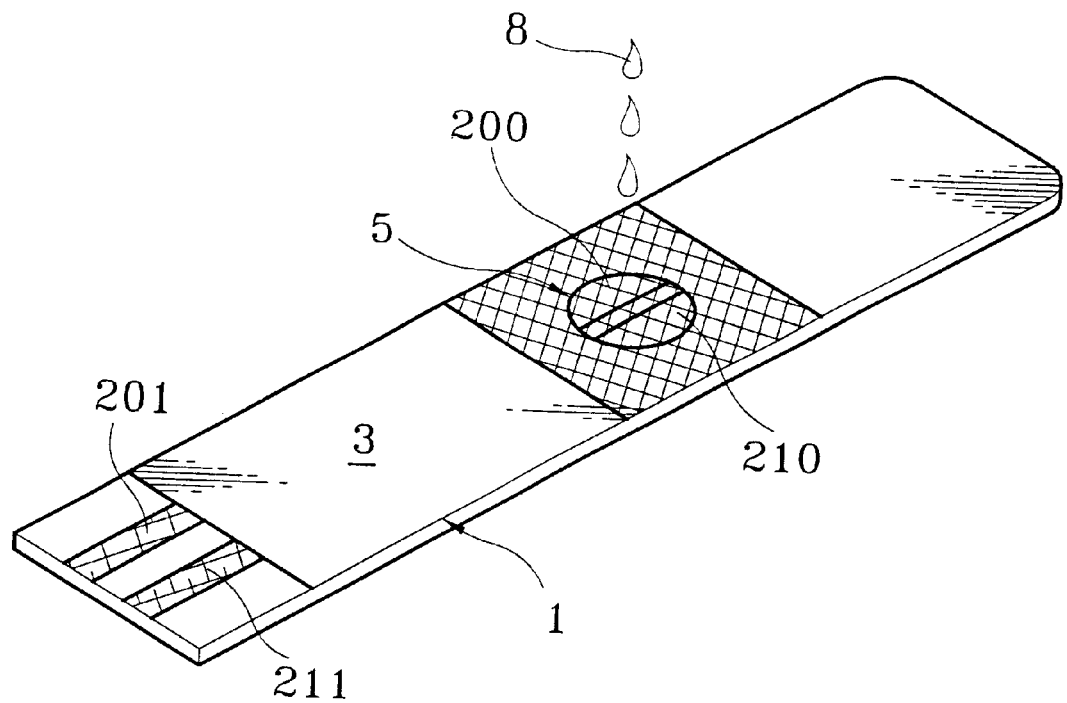
Figure 4G:
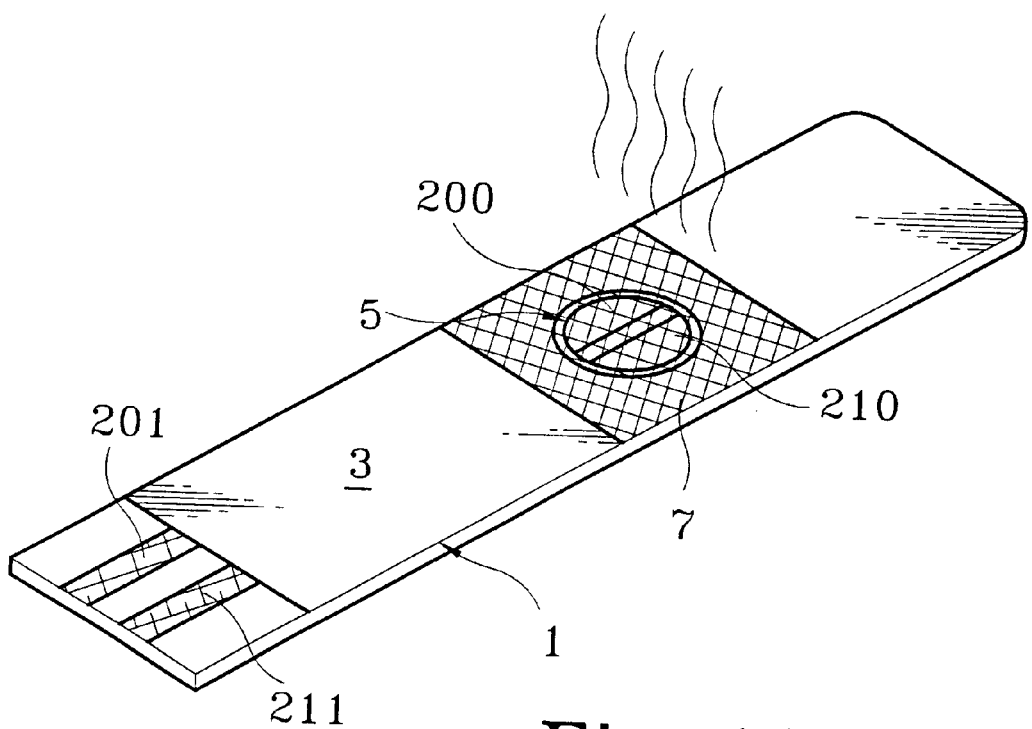
Figure 4H:
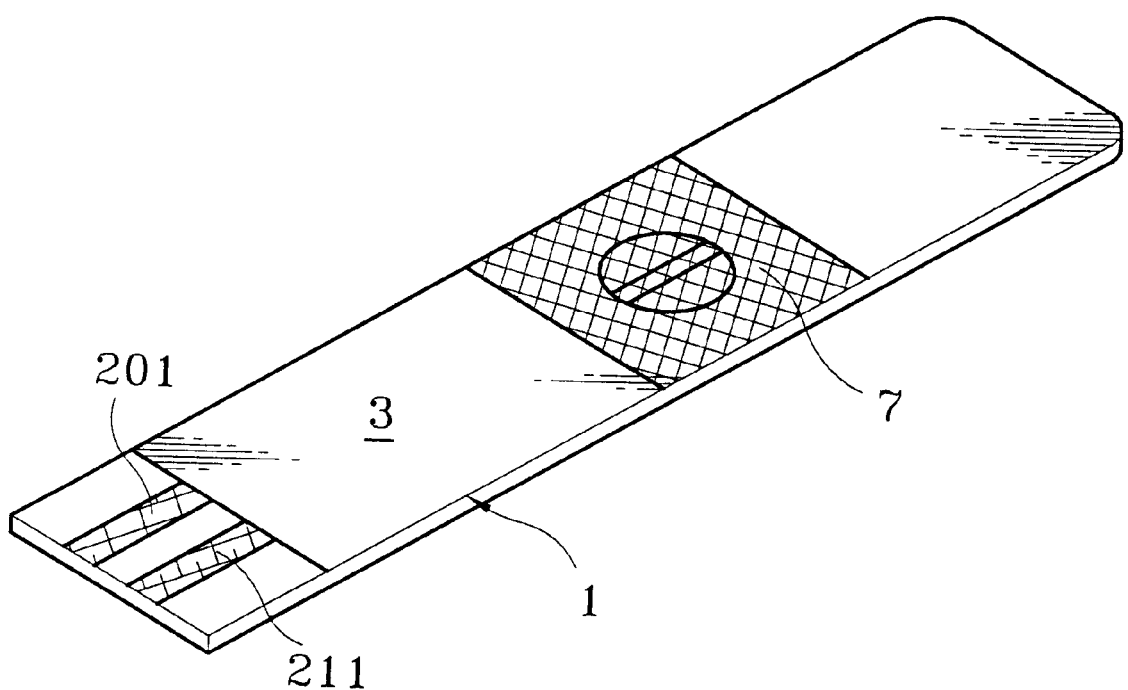

As shown in FIG. 1 and FIG. 2, an approximate strip type plate electrode is advantageous for loading a test sample 6 and suitable for use in the following manufacture method. The plate electrode, according to the cutaway sectional view in FIG. 3, comprises: a strip substrate 1 with plane surface, a conductive film 2 located on one surface of the substrate 1, an electric insulating layer 3 locally covering the conductive film 2, and, a biological active layer 4 covering the bare portion of the conductive film 2, which, the biological active layer 4, doesn't overlap the electric insulating layer 3 thoroughly.

In addition to the plane surface, the foregoing substrate 1 must be meanwhile an electric insulator and a heat resister capable of enduring 40° C.~120° C. heat treatment in order to increase conductivity and adherence of the conductive film 2. The applicable materials for the substrate 1 include PVC (Polyvinyl Chloride), FRP (Fiber Reinforced Plastics, FR-4), Polyester sulfone, Bakelite, PET, PC, glass, or ceramics (CEM-1), etc.

The conductive film 2 comprises at least a pair of separated electrodes, namely, an anode 20 and a cathode 21 to connect with a sensor. One of two bare ends of the anode 20 is a work electrode 200 covered with the biological active layer 4, and the other is an anode coupling 201, wherein the work electrode 200 is used to detect the electric effect induced by chemical or biochemical reaction of the test sample 6, and the anode coupling 201 is used to connect with the sensor as mentioned. As to two bare ends of the cathode 21, one end is a reference electrode 210 covered with the biological active layer 4, and the other is a cathode coupling 211 in arbitrary shape. The reference electrode 210 is used to cooperate with the work electrode 200 for detecting electric effect of the test sample 6, while the cathode coupling 211 is used to connect with the sensor.

The electric insulating layer 3 is coated on the same surface of the substrate 1 at 0.6 mm thick or up without covering the anode coupling 201, the cathode coupling 211, the work electrode 200, and the reference electrode 210 to form a circular area on the work electrode 200 and the reference electrode 210, namely, the space of biological active layer 4, for placing a biological active substance or the test sample 6.

This invention is characterized by providing a distinguishing biological active layer 4 in order to simplify production process of the plate electrode and also to raise its quality. The biological active layer 4 comprises: a carrier 5 printed on the work electrode 200 and the reference electrode 210 by screen-printing technique, a net protector 7 shading on the work electrode 200 and the reference electrode 210, as well as the biological active substance adsorbed by the carrier 5, and the conductive mediator.

The aforesaid carrier 5 is a blended paste for screen-printing, and the ingredients thereof may include:

1. Microcrystalline cellulose with grain size at 100 $\mu$m down, 10~40% adulterated.
2. High molecule polymer with 10~25% adulterated, such as PVA (Polyvinyl alcohol), PVP (Polyvinyl pyrrolidone), PEG (Polyethylene glycol), or gelatin. Each single item or blended may be used.
3. Salt adulterated at 1~5%, such as Dibasic potassium phosphate, Potassium biphosphate, and Citric acid. The salt is used to adjust pH value and serve as a buffer solution. The proper range of pH value is 4.5~9.0.
4. Water. Pure water undergone at least one time distillation would be a must.

Embodiment 1:

| | |
|---|---:|
| Microcrystalline cellulose (grain size 20~100 $\mu$m) | 20% |
| PVA | 3.5% |
| PVP | 2.8% |
| PEG | 12% |
| Gelatin | 2.1% |
| Dibasic potassium phosphate | 0.7% |
| Citric acid | 1.5% |
| Water | 57.4% |

Embodiment 2:

| | |
|---|---:|
| Microcrystalline cellulose (grain size 20 $\mu$m down) | 35% |
| PVA | 13% |
| PVP | 7% |
| Dibasic potassium phosphate | 0.7% |
| Citric acid | 1.5% |
| Water | 42.8% |

Embodiment 3:

| | |
|---|---:|
| Microcrystalline cellulose (grain size 20 $\mu$m in average) | 21.2% |
| PEG | 19.8% |
| Dibasic potassium phosphate | 0.7% |
| Citric acid | 1.5% |
| Water | 56.8% |

Embodiment 4:

| | |
|---|---:|
| Microcrystalline cellulose (grain size 20 $\mu$m in average) | 21.2% |
| PVP | 13.4% |
| PEG | 0.3% |
| Dibasic potassium phosphate | 0.04% |
| Potassium biphosphate | 0.1% |
| Water | 64.96% |

The carrier 5 is coated on surface of the circular area of the work electrode 200 and the reference electrode 210 for adsorbing a biological active substance and conductive mediator to change the carbon electrodes from hydrophobic into hydrophilic for strengthening adsorption of the test sample and to assure the biological active substance will not be impaired in relatively high temperature drying process, so that the yield of the plate electrode may be raised up. The biological active substance means immobilized or unimmobilized enzyme (such as Glucose Oxidase), antigen, antibody, microbe cell, and cell or tissue of animals or plants, which possess biologically discriminative constituents, for use to react with a test sample (biological tissue such as blood) chemically or biochemically. The conductive mediator (such as potassium ferricyanide, quinones) at content ratio 2~10% is used to receive the electrons released from the reaction between an enzyme and a test sample, which, the electrons, will be transmitted to the sensor via a conductor to transfer into concentration of the test sample.

The biological active substance must be mixed with the conductive mediator, the composition is listed as the following:

1. Enzyme, such as Glucose Oxidase with dosage 200 U~1200 U/ml.

2. Enzyme protector with dosage 0.1~1%, including: albumin, dextrin, dextran, or amino acid, which can be used independently, or in blended.
3. Conductive mediator with dosage 2~10%, such as Potassium ferricyanide.
4. Phosphate buffer solution at pH 4.8~7.5.

Embodiment 5:

| | |
|---|---|
| Glucose Oxidase | 0.63% |
| Albumin | 0.5% |
| Potassium ferricyanide | 6% |
| Phosphate buffer solution at pH 5.0 | 92.87% |

Embodiment 6:

| | |
|---|---|
| Glucose Oxidase | 0.45% |
| Albumin | 0.5% |
| Dextran | 0.01% |
| Potassium ferricyanide | 4.8% |
| Phosphate buffer solution at pH 7.4 | 94.24% |

Embodiment 7:

| | |
|---|---|
| Glucose Oxidase | 0.63% |
| Albumin | 0.5% |
| Glutamic acid | 0.3% |
| Potassium ferricyanide | 6% |
| Phosphate buffer solution at pH 7.0 | 94.57% |

Embodiment 8:

| | |
|---|---|
| Glucose Oxidase | 0.21% |
| Dextrin | 0.39% |
| Glutamic acid | 0.3% |
| Potassium ferricyanide | 3.8% |
| Phosphate buffer solution at pH 5.1 | 95.3% |

As shown in FIG. 4A through FIG. 4H—the production flow charts of this invention, the procedure includes the following steps:

1. Please refer to FIG. 4A. To print at least one layer conductive film 2 with screen printing technique including at least an anode and a cathode. The material of the conductive film 2 can be a carbon paste, silver plasma, mixed plasma of carbon and silver, volatile graphite, or copper paste, which can be used independently or in pack (for example, printing the carbon paste after the silver plasma), then heated at 40° C.~120° C. for drying.
2. Please refer to FIG. 4B. To print an electric insulating layer 3 at least in 0.6 mm thick on the same face with the printed conductive film 2 by using screen printing technique, except some bare area reserved for forming the anode coupling 201, cathode coupling 211, work electrode 200, and reference electrode 210. A circular area formed by the work electrode 200 and the reference electrode 210 is called the area of biological active layer.
3. Please refer to FIG. 4C. To print a layer of the cellulose carrier on the circular area of the biological active layer with screen printing technique.
4. Please refer to FIG. 4D. To dry the carrier 5 in room temperature (20° C.~30° C.).
5. Please refer to FIG. 4E. To coat the surface surrounding the circular area of the biological active layer with glue 70 and have the net protector 7 adhered to cover the carrier 5 as mentioned in step 3.
6. Please refer to FIG. 4F. To drip the buffer solution 8 containing the biological active substance and conductive mediator into the carrier 5 in the circular area, where the buffer solution 8 will be absorbed by cellulose of the carrier 5.
7. Please refer to FIG. 4G. To dry the plate electrode made according to step 6 in ambient temperature at 40° C.~60° C. to complete the manufacture process as shown in FIG. 4-H.

From above description, it is understood that this invention provides a relatively speedy manufacture process for plate electrode by virtue of coating the cellulose layer of carrier on the biological active layer to adsorb the biological substance and conductive mediator, so that the work electrode and the reference electrode can be changed from hydrophobic into hydrophilic, and the biological substance can be protected against impairment in subsequent manufacture process, and moreover, the screen printing method facilitates a high production yield.

Although, this invention has been described in terms of preferred embodiments, it is apparent that numerous variations and modifications may be made without departing from the true spirit and scope thereof, as set forth in the following claims.

What is claimed is:

1. A disposable plate electrode, comprising:
   a plane substrate;
   a conductive film disposed on one of two relative larger surfaces of said substrate and comprising at least a pair of elongated separated electrodes forming an electrode pair comprising an anode and cathode;
   an electric insulating layer partially covering said electrode pair and leaving both ends of said electrode pair uncovered to form a first end pair and a second end pair;
   the first end pair forming a work electrode and a reference electrode which pair is covered with a biological active layer containing a cellulose carrier having adsorbed therein a biological active substance which reacts chemically or biochemically with a test sample; and
   the second end pair forming a connector for a sensor for said test sample;
   wherein said carrier is a blended paste suitable for screen printing and includes microcrystalline cellulose, a high molecular polymer which is polyvinyl alcohol, polyvinyl pyrrolidone, polyethylene glycol, gelatin or a mixture thereof; salt and water.

2. The disposable plate electrode of claim 1, wherein said substrate is formed of a board of PVC, FRP (FR-4), Polyester sulfone, Bakelite, PET, PC, Glass, or ceramics (CEM-1).

3. The disposable plate electrode of claim 1, wherein grain size of said microcrystalline cellulose is 100 $\mu$m or less.

4. The disposable plate electrode of claim 1, wherein said salt is dibasic potassium phosphate, potassium biphosphate or a salt of citric acid, which salts provide a pH value adjustment in a range of from 4.5~9.

5. The disposable plate electrode of claim 1, wherein the water is pure and has been distilled at least to one time.

6. The disposable plate electrode of claim 1, wherein said biological substance comprises an immobilized or enzyme, antigen, antibody, microbe cell, animal or plant cell, animal or plant tissue which possesses biological cognizable properties for chemical or biochemical reaction when contacted with a test sample.

7. The disposable plate electrode of claim 1, wherein said conductive mediator comprises potassium ferricyanide.

8. The disposable plate electrode of claim 6, wherein said biological active substance is blended with said conductive mediator.

9. The disposable plate electrode of claim 8, wherein the blended biological active substance and conductive mediator comprises a composition comprising an enzyme, enzyme protector, conductive mediator and phosphate buffer solution.

10. The disposable plate electrode of claim 9, wherein said enzyme is concentrated at 200 U~1200 U/ml.

11. The disposable plate electrode of claim 9, wherein the enzyme protector is present in an amount of from 0.1%~1% and is selected from the group consisting of albumin, dextrin, dextran, amino acid and a mixture thereof.

12. The disposable plate electrode of claim 9, wherein said conductive mediator comprises from about 2%~10% potassium ferricyanide.

13. The disposable plate electrode of claim 9, wherein said phosphate buffer has a pH of 4.8~7.5.

* * * * *